United States Patent [19]

Jacquet et al.

[11] Patent Number: 4,608,392
[45] Date of Patent: Aug. 26, 1986

[54] METHOD FOR PRODUCING A NON GREASY PROTECTIVE AND EMOLLIENT FILM ON THE SKIN

[75] Inventors: Bernard Jacquet, Antony; Quintino Gaetani, Bondy, both of France

[73] Assignee: Societe Anonyme dite: L'Oreal, Paris, France

[21] Appl. No.: 645,156

[22] Filed: Aug. 28, 1984

[30] Foreign Application Priority Data

Aug. 30, 1983 [LU] Luxembourg .................. 84979

[51] Int. Cl.$^4$ .................................. A61K 47/00
[52] U.S. Cl. ................................. 514/844; 8/405;
  8/406; 424/DIG. 4; 424/59; 424/60; 424/63;
  424/68; 424/69; 424/70; 424/73; 514/165;
  514/167; 514/199; 514/251; 514/420; 514/458;
  514/474; 514/725; 514/846; 514/847; 514/859
[58] Field of Search ................ 424/59, 239, 342;
  514/846, 841, 772, 63, 941, 847, 844

[56] References Cited

U.S. PATENT DOCUMENTS

| | | | |
|---|---|---|---|
| 3,758,595 | 9/1973 | Lamberti et al. | 568/37 |
| 3,988,377 | 10/1976 | Lamberti et al. | 568/37 X |
| 4,105,580 | 8/1978 | Sebag et al. | 568/37 |
| 4,171,455 | 10/1979 | Tomita et al. | 424/342 |
| 4,303,639 | 12/1981 | Vanlerberghe et al. | 424/65 |
| 4,465,860 | 8/1984 | Vanlerberghe et al. | 568/37 |
| 4,486,406 | 12/1984 | Abe et al. | 424/342 |

FOREIGN PATENT DOCUMENTS

| | | | |
|---|---|---|---|
| 0011237 | 5/1980 | European Pat. Off. | 424/341 |
| 894110 | 10/1953 | Fed. Rep. of Germany | 568/560 |
| 1255235 | 11/1967 | Fed. Rep. of Germany | 514/844 |
| 3026448 | 2/1982 | Fed. Rep. of Germany | 424/342 |
| 3121139 | 12/1982 | Fed. Rep. of Germany | 568/560 |
| 2364196 | 4/1978 | France | 568/560 |
| 0051035 | 4/1977 | Japan | 424/70 |
| 00083606 | 5/1983 | Japan | 424/70 |

OTHER PUBLICATIONS

Hobin, Chemical Abstracts, 12/1965, vol. 63, No. 13, p. 17879.

*Primary Examiner*—Dale R. Ore
*Attorney, Agent, or Firm*—Cushman, Darby & Cushman

[57] ABSTRACT

A composition for topical application to the skin contains, as a fatty product to provide a nongreasy protective and emollient film thereon, a polyether oligomer having the formula

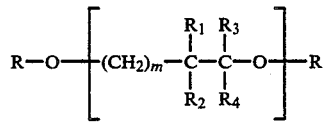

wherein R is alkyl having 1-12 carbon atoms; $R_1$, $R_2$, $R_3$ and $R_4$ represent hydrogen or alkyl having 1-6 carbon atoms, with at least two of $R_1$, $R_2$, $R_3$ and $R_4$ being hydrogen; m is 1-4; n has an average value equal to or greater than 2; and the number of carbon atoms in each repetitive unit being at least 4.

7 Claims, No Drawings

METHOD FOR PRODUCING A NON GREASY PROTECTIVE AND EMOLLIENT FILM ON THE SKIN

The object of this invention is new cosmetic or pharmaceutical composition, in aqueous or anhydrous form, containing, as a fatty product, at least one polyether oligomer either alone or in a mixture with other fatty products such as oils, fats or waxes.

Both natural and synthetic oils form a very large class of substances which are used in a wide variety of cosmetic of pharmaceutical compositions, as a medium or excipient.

In general, the oils in these compositions are not used alone but in a mixture with other oils or fatty products such as fats and waxes, wherein the proportions of these fatty substances are a function either of the consistency or of the properties to be produced.

Until now, few disclosures have been made for oils which are appropriate both for the formulation of either cosmetic compositions or pharmaceutical compositions.

Indeed, apart from a few natural or synthetic oils, including liquid paraffin, at this time, there exists no class of substances displaying all of the criteria required for such a product to be used equally well as fatty media or excipients in cosmetics and pharmaceuticals.

For use in cosmetics, the oils must spread easily and leave a hydrophobic film on the skin without stickiness or a greasy appearance; they must also display emollient properties, that is, softening, lubricating and nourishing properties in order to maintain the elasticity of the skin and to protect it from damage from the elements.

For pharmaceutical applications, the most sought after properties for oils are high solubility for various active ingredients as well as stability and stabilizing effects on these substances when exposed to heat, light and oxygen in the air.

These latter properties may also be of interest for cosmetics when the compositions contain certain substances that are beneficial to the skin or other substances used as ingredients in these compositions such as, for example, fragrances, coloring agents, pigments, preservatives, etc.

It has now been observed that these properties could be obtained by using a certain class of polyether oligomers which are liquid at ambient temperature and insoluble in water.

By virtue of their excellent properties, these polyethers (some of which are known) can be used equally well in cosmetic or pharmaceutical products without the disadvantages of the compounds which have been used until now, that is, a greasy feel and low solubility.

One property of these polyether oligomers which is of special interest is the fact that they leave on the skin a matte film, which is not greasy to the touch, and provides protection and an emollient effect.

The object of this invention is a new industrial product comprising an aqueous anhydrous cosmetic or pharmaceutical composition which contains, as a fatty product, at least one polyether oligomer which is liquid at ambient temperature and insoluble in water, of the following formula:

$$R-O-\left[-(CH_2)_m-\underset{\underset{R_2}{|}}{\overset{\overset{R_1}{|}}{C}}-\underset{\underset{R_4}{|}}{\overset{\overset{R_3}{|}}{C}}-O-\right]_n R \quad (I)$$

wherein:
R represents an alkyl radical, which may be either linear or branched, containing from 1 to 12 carbon atoms:
$R_1$, $R_2$, $R_3$ and $R_4$ may be either identical or different, and represent a hydrogen atom or an alkyl radical containing from 1 to 6 carbon atoms, wherein at least two of the $R_1$, $R_2$, $R_3$ or $R_4$ radicals represent a hydrogen atom,
m is a number from 1 to 4,
and n is an average value $\geq 2$ and preferably between 4 and 50,
the number of carbon atoms in each repetitive unit, whether identical or different, is at least equal to 4.

In the polyether oligomers of Formula (I), the R radical preferably represents a methyl, ethyl, butyl, hexyl or lauryl radical.

The average value of the molecular weight of these compounds generally ranges from 200 to 5,000 and their viscosity ranges from 2 to 1,000 centipoises measured at 25° C. and preferably ranges from 10 to 100 centipoises.

Among the polyether oligomers of Formula (I) which are preferred for implementing the compositions according to the invention, those wherein the R radical represents a methyl, ethyl or butyl radical, the $R_1$ to $R_4$ radicals represent a hydrogen atom and m is equal to 2, can more specifically be mentioned.

The compound which is specifically preferred, and has produced excellent results both in cosmetic and pharmaceutical applications, is dimethyl ether of polytetrahydrofuran, of the following formula:

$$CH_3-O-[-(CH_2)_2-CH_2-CH_2-O-]_n CH_3$$

where n is an average value between 4 and 10 inclusive.

The polyether oligomers of Formula (I) display good compatibility with numerous fatty substances, whether mineral, vegetable, animal or synthetic oils. In addition, they are soluble in a large number of common organic solvents normally employed in cosmetic or pharmaceutical compositions.

More particularly, the polyether oligomers of Formula (I) can advantageously replace in U.S. Pat. No. 4,335,046 the volatile siloxanes such as hexamethyl disiloxane, octamethyl cyclotetrasiloxane and decamethyl cyclopentasiloxane in order to improve the cosmetic properties of the fractions termed "solid fractions" of petrolatum, that is, fractions containing no liquid petrolatum or at most 20% by weight.

In comparison with U.S. Pat. No. 4,355,046, the mixtures of the solid fractions of the petrolatum and the polyether oligomers of Formula (I) do not produce a sticky effect when applied and provide good cosmetic properties which are very close to those of petrolatum but without its disadvantages, that is, primarily, its irritant effect on the skin.

As mentioned above, some of the polyether oligomers are known; nonetheless, certain details on the processes for obtaining these shall be provided below.

The most advantageous process consists of obtaining these from cyclic ethyloxides through a cationic copolymerization or polymerization reaction in the presence of an ester of orthoformic acid and a polymerization catalyst.

Among the cyclic ethers that may be used produce polyether oligomers of Formula (I), wherein the radical m=1, the following may be cited: methyl-2 oxetane, methyl-3 oxetane, dimethyl-2,3 oxetane, dimethyl-3,3 oxetane and butyl-3 ethyl-3 oxetane.

Among the cyclic ethers that may be used to produce polyether oligomers of Formula (I), wherein the radical m=2, the following may be cited: tetrahydrofuran, methyl-2 tetrahydrofuran, methyl-3 tetrahydrofuran and ethyl-2 tetrahydrofuran.

Among the cyclic ethers that may be used to produce polyether oligomers of Formula (I), wherein the radical m=4, oxepane and its substituted derivatives may be cited.

Since this results from the general Formula (I) of polyether oligomers, repetitive units may be either identical or different and, in the latter case, there are, more specifically, copolymers.

Indeed, although most of the cyclic ethers mentioned above can be homopolymerized, some of them can only be copolymerized, as in the case, for instance, of methyl-2 tetrahydrofuran.

In this case, methyl-2 tetrahydrofuran is copolymerized with tetrahydrofuran, for example, which explains why the repetitive units of the polyether oligomers in the same compound may be of different structures.

The ester of orthoformic acid produces a transfer reaction which can limit molecular weights and produce the terminal ether functions.

As an ester of orthoformic acid, the following may be cited: methyl orthoformate, ethyl orthoformate, isopropyl orthoformate, butyl orthoformate, etc.

The quantity of the ester of orthoformic acid in the polymerization reaction is variable and depends on the molecular weight of the polyether oligomer to be produced, but it generally ranges from 5 to 500% relative to the weight of the initial cyclic ethyl oxide.

The polymerization catalyst may be any one of the cationic polymerization catalysts such as boron trifluoride etherates, the complexes $BF_3$-epichlorhydrine $SnCl_4$-epichlorhydrine, $AlEt_3$-$H_2O$-epichlorhydrine, triethyloxonium salts such as $Et_3O^+BF_4^-$, $Et_3O^+sbCl_6^-$, $Et_3O^+PF_6^-$, p-chlorophenyldiazonium salts such as p-$ClC_6H_4N_2PF_6$ or trifluoromethane sulfonic acid and its derivatives such as its anhydride and its esters.

The quantity of catalyst normally ranges from 1 to 5% relative to the total weight of the reactants used.

The temperature and the polymerization time are available depending on the nature of the cyclic ether used at the outset.

In the case of tetrahydrofuran, the polymerization reaction is generally carried out at ambient temperature, for a period ranging from 4 to 10 hours.

After deactivation of the catalyst and removal of the volatile substances, the polyether oligomer obtain may potentially be purified using various conventional processes, for example, using carbon black.

The polyether oligomers may also be obtained by other processes, for instance from an oligomer in the form of diol or dihalogenide and by subsequently forming the terminal ether function according to conventional methods.

In the compositions according to the invention, the polyether oligomer of Formula (I) may be present in variable proportions, as its concentration is a function of the nature of the composition; however, it generally ranges from 0.5 to 99% by weight relative to the total weight of the composition and preferably ranges from 5 to 50%.

The polyether oligomer may be used alone or in a mixture with other fatty substances such as vegetable or animal oils, mineral oils or synthetic oils, and may constitute the oil phase of various cosmetic or pharmaceutical compositions.

In addition, the oil phase may also contain a certain proportion of wax or of fat.

Among the modified or unmodified vegetable or animal oils, the following may be cited as examples: oil of sweet almond, avocado oil, castor oil, olive oil, jojoba oil, palm oil, perhydrosqualene, calophyllum oil, lanolin and its derivatives, purcellin oil, grape seed oil, sesame oil, and soybean oil.

Among the synthetic oils, esters may be cited, such as ethyl and isopropyl palmitate, alkyl myristates such as isopropyl, butyl, cetyl myristate, hexyl stearate, triglycerides of octanoic and decanoic acids (for example, the product sold under the trade name "Miglyol 812" by the Dynamit Nobel company), cetyl ricinoleate, stearyl octanoate, hydrogenated polyisobutene and silicone which are soluble in other oils such as, for example, dimethylpolysiloxane or methyl phenyl polysiloxane.

Among the mineral oils, oil of petrolatum may be cited.

Among the waxes, the following may particularly be cited: carnauba wax, beexwax, ozokerite, candelilla was, montan wax and the microcrystalline waxes.

These oils and waxes, which are commonly used not only in cosmetics but also in pharmaceutical applications, constitute substances which are suitable for use in producing the oil phases or oils in various products.

The oil phase of the compositions according to the invention constitutes from 3 to 99% and preferably 8 to 90% by weight of the total weight of the composition.

Among the cosmetic compositions, those which are displayed in the form of liquid emulsions (lotions) or thicker emulsions (creams) can more specifically be cited, in the form of lotions, solutions or suspensions, anhydrous salves, sticks, gels, etc.

These compositions are, for example, lotions or creams for the face, hands or body, masks, cleansing creams or lotions, make-up products, "suntan" lotions, oils or creams, artificial tanning lotions or creams, antiperspirant lotions or creams, shaving or cleansing creams or foams, hair treatment products such as shampoos, rinses, lotions for application before or after shampooing, coloring or bleaching compositions, etc.

When the compositions are displayed in the form of creams or lotions, these are, more specifically, emulsions of the water-in-oil or oil-in-water type, the oil phase of which represents 4 to 60% by weight, the water phase, 30 to 60% by weight and the emulsifying agent, 1 to 20%, preferably 2 to 12% by weight.

Among the emulsifying agents, the following may more specifically be cited:
the polyoxyethylenated or polyglycerolated fatty alcohols, the oxyethylenated or non oxyethylenated alkyl sulfates, mixtures of at least one lanolate such as magnesium, calcium, lithium, zinc or aluminum lanolates and hydrogenated lanolin and/or lanolin alcolhol, the esters of fatty acids and of polyols such as glycerol or propylene glycol;

the monoesters of fatty acids and of polyoxyethylene sorbitans, for instance, the product sold by the ATLAS company under the trade name "Tween."

These compositions may also contain other conventional ingredients such as thickeners or gelling agents such as, for example:

magnesium and aluminum silicates;

methyl vinyl ether/maleic anhydride copolymers such as the products sold under the trade name "Viscofas X 100000" or "Viscofas L. 100" by the ICI company, which may potentially be neutralized;

or carboxyvinyl polymers such as the products sold under the trade name "Carbopol" by the Goodrich company;

or alcoyl polyglutamates such as those disclosed in U.S. Pat. No. 3,285,953.

The cosmetic compositions may also contain various other ingredients such as, in particular, coloring agents, fragrances, preservatives, U.V. filtering agents, pigments, iridescent agents, mineral or organic fillers, active ingredients, surface-active agents, solvents or protective agents.

Among the active ingredients, the following may be cited: anti-acne and anti-seborrhea substances such as broparoestrol, benzoyl peroxide, 13-cis retinoic acid and thioxolon; moisturizing agents such as monoethylic ether of diethylene glycol, lanolin, magnesium lanolate, thiomorpholinone-3 and its derivatives, lactic acid; and vitamins, such as vitamins A, C, D2 and E.

The pharmaceutical compositions are, for example, creams, ointments, salves and, in general, all compositions used topically and the excipient of which contains a fatty substance.

The polyether oligomers of Formula (I) are, in fact, excellent excipients for a very large number of active substances because of their particularly high solubility.

Among the active substances with therapeutic effects, the following may be cited:

anti-inflammatory agents such as 18-glycyrrhetinic acid, hydrocortisone, hydrocortisone acetate, hydrocortisone butyrate, hydrocortisone t-butyl acetate, dexamethasone and its acetic esters and acetic t-butyl, salicylic acetyl acid, flufenamic acid and indomethacetin.

Indomethacetin, when combined with the polyether oligomers of Formula (I), in a concentration of 0.5 to 5%, provides for preparation of compositions in the forms of salves, gels or creams which are very efficient in topical treatment of dermatosis.

antibiotics such as tetracycline, erythromycin and other macrolides or neomycin;

antiseptics such as trichloro-2,4,4'-hydroxy-2'diphenyl ether known under the trade name of "IRGASAN DP 300", hexachlorophene, iodine, etc.;

keratolytics such as salicylic acid, resorcinol, etc.;

antifungal agents such as griseofulvin, tolnaphtate;

anti-psoriasis agents such as anthralin, its dimer and its derivatives.

Although the compositions according to the invention display good stability over periods of time, this stability may be improved by the addition of certain antioxidants such as, for example, butylated hydroxyanisole (BHA) or butylated hydroxytoluene (BHT), or a mixture of these substances containing approximately 0.002 to 0.2% of antioxidant in relation to the total weight of the composition.

Several non-limiting examples of the preparation of polyether oligomers of Formula (I), and several examples of cosmetic and pharmaceutical compositions using these compounds as a base shall now be provided for purposes of illustration.

EXAMPLES OF PREPARATIONS

Example 1

Preparation of dimethyl ether from polytetrahydrofuran with a viscosity of 22 cp In a 20 liter reactor equipped with an agitator, a cooler, a thermometer and a nitrogen intake, 5.32 kg of distilled tetrahydrofuran and 5.8 kg of distilled methyl orthoformate (or 109% relative to the tetrahydrofuran) are introduced.

The mixture is then agitated under nitrogen and cooled to 13° C.

120 ml of sulfonic trifuloromethane anhydride are added to initiate polymerization. After 4 hours at 18°-20° C., the catalyst is deactivated using 120 g of pure soda in solution in 600 ml of ionized water. The volatile products are then expelled under vacuum at 80° C. After cooling, 6 liters of distilled cyclohexane and 120 mg of powdered carbon black are introduced. The mixture is agitated for 1 hour, then filtered by rinsing the precipitate with distilled cyclohexane.

The filtrate is then agitated under vacuum at 50° C., then at 80° C. and finally at 100° C. to eliminate the solvent and the volatile polyether fractions. 3.75 kg of an oily, colorless compound are thus recovered. Elemental analysis, infrared spectroscopy and RMN spectroscopy show that the formula of the compound is the following:

$$CH_3-O-[(CH_2)_2-CH_2-CH_2-O]_{\overline{n}}CH_3$$

and that its average molecular weight, determined by tonometry, is 410+20, which corresponds to a value for n on the order of 5.

The oil produced displays a dynamic viscosity at 25° C. of 22 cp and solidifies at −1° C. It is soluble in the usual organic solvents such as alcohol, acetone, benzene, hexane, chloroform and is insoluble in water.

This oil is miscible in any proportion with oil of petrolatum, avocado oil or perhydrosqualene.

Example 2

Preparation of dimethyl ether from polytetrahydrofuran with a viscosity of 34 cp Polymerization is performed under the same conditions as those described in Example 1 above, but using 4.34 kg of tetrahydrofuran, 3.87 kg of methyl orthoformate (or 89% in relation to the tetrahydrofuran) and 89 ml of sulfonic trifluormethane anhydride. The catalyst is deactivated using the same proportion of soda and the product is purified in the same way, by filtration in the presence of carbon black, then drying under vacuum. 2.76 kg of an oily, colorless compound are produced, displaying the same structure as the compound of Example 1. Its dynamic viscosity at 25° C. is 34 cp and its solidification point is +2° C. (average value of n≃5).

Example 3

Preparation of dimethyl ether from polytetrahydrofuran with a viscosity of 40 cp The polymerization is again performed according to the same procedure as in Example 1, but using 5.32 kg of tetrahydrofuran, 3.86 kg of methyl orthoformate (or 72.5% in relation to the tetrahydrofuran). The reaction is catalyzed using 100 mg of sulfonic trifluormethane anhydride. After four hours of reaction time, the catalyst is deactivated using 100 g of soda. After processing with carbon black and drying, 3.49 kg. of the expected oily, colorless compound is obtained, with a dynamic viscosity at 25° C. of 40 cp and a solidification point of +3° C. (average value of n≅5).

Example 4

Preparation of dimethyl ether from polytetrahydrofuran with a viscosity of 91 cp In a 2 liter reactor, 576.5 g of tetrahydrofuran, 338.5 g of methyl orthoformate (or 58.7% in relation to the tetrahydrofuran) and 10 ml of sulfonic trifluoromethane anhydride are introduced to initiate the polymerization reaction.

After four hours of reaction time, the catalyst is deactivated by 15 g of soda. After a first drying under vacuum, 500 ml of distilled cylohexane are added and filtered on a clay bed (Celite 545). After evaporation of the cyclohexane, the product is dried in a vacuum at 80° C. then at 130° C. 390 g of a viscous, colorless liquid are produced, having the same chemical structure as the compounds produced in accordance with the previous examples.

Its dynamic viscosity at 25° C. is 91 cp and its solidification point is +11° C. (average value of n≅6–7).

Example 5

Dimethyl ether from the copolymer methyl-2 tetrahydrofuran/tetrahydrofuran with a viscosity of 164 cp In a 250 ml three-neck flask equipped with a thermometer, a nitrogen intake and a septum, 43.8 g of tetrahydrofuran, 10.7 g of methyl-2 tetrahydrofuran and 3.2 g of methyl orthoformate (5.8% in relation to the monomers) are introduced.

The mixture is brought to 0° C. under nitrogen and, using a syringe, 1.1 g of sulfonic trifluoromethane anhydride are added. After six hours of agitation at 0° C., 2 g of powdered sodium methanolate are used for deactivation. The volatile compounds are evaporated under vacuum, then the residue is recovered in 50 ml of cyclohexane. The non-soluble matter is then filtered and the solvent expelled under vacuum. Drying is completed at 80° C. under vacuum, for one hour. 17.7 g of an oily compound are thus obtained, displaying a dynamic viscosity at 25° C. of 164 cp and a solidification point of +7°–8° C.

IR and RMN spectroscopic analysis indicates the presence in the chain of units derived from polymerization of methyl-2 tetrahydrofuran. The ratio of units derived from methyl-2 tetrahydrofuran relative to those derived from tetrahydrofuran is 5.7/94.3, according to RMN analysis (average value of n≅10).

Example 6

Dimethyl ether from the copolymer methyl-2 tetrahydrofuran/tetrahydrofuran with a viscosity of 9.7 cp The same procedure as in Example 5 above is followed, but using 40.4 g of methyl orthoformate or 74% in relation to the total weight of the monomers.

After deactivation and processing as described in that example, 29.1 g of a liquid oligomer are obtained and display a dynamic viscosity of 9.7 cp at 25° C. and a solidification point of −15° C.

The ratio of units derived from methyl-2 tetrahydrofuran to those derived from tetrahydrofuran is 6.6/93.4 according to RMN analysis and the average value of n is approximately 3.2.

Example 7

Dibutyl ether from polytetrahydrofuran with a viscosity of 15 cp

In a 250 ml three-neck flask equipped with a nitrogen intake, a thermometer and a septum, 50 g of tetrahydrofuran and 100 g (200% in relation to the monomer) of butyl orthoformate are introduced. The mixture is brought to 25° C. and 2 ml of sulfonic trifluormethane anhydride are introduced using a syringe. It is agitated for 5 hours at 25° C. then deactivated using 3 g of powdered sodium methanolate. The volatile compounds are expelled at 80° C. under 1 to 2 mm of Hg then 100 ml of hexane are added, the insoluble product is filtered and the solvent is evaporated under vacuum.

After drying for two hours at 90° C. under 1 to 2 mm of Hg, 20 g of an oily, light yellow compound are obtained. RMN analysis confirms the expected structure of the polyether, with an average value for n of 5.4.

The dynamic viscosity of the oil produced is 15 cp at 25° C.; it solidifies between −8° C. and −10° C.

Example 8

Dimethyl ether from poly(methyl-2-trimethylene oxide) with a viscosity of 115 cp In a 25 ml reaction tube equipped with a nitrogen intake and a septum, 7.4 mg of methyl-2 oxetane are introduced (Eb 760 mm=60°–61° C.) prepared by cyclization of butanediol 1-3.

5.1 g of methyl orthoformate are added (or 68.9% in relation to the monomer).

The mixture is cooled at +5° C. in an ice bath then, using a syringe, 0.5 ml of boron trifluoride etherate are inserted. After agitation, the reaction tube is kept in the ice bath for 6 hours. The mixture is deactivated using 2 g of powdered sodium methanolate and recovered using 15 ml of hexane.

The insoluble product is filtered, the volatile products are eliminated under vacuum and drying is completed at 80° C. under 1-2 mm of Hg. 7.4 g of the expected oligomer are obtained (structure confirmed by IR and RMN). The polyether is liquid, colorless, insoluble in water, and displays a dynamic viscosity of 115 cp; it remains liquid up to a temperature of −35° C.

Example 9

Dimethyl ether from polytetrahydrofuran or dimethoxy-4,4' dibutyl ether of formula CH$_3$—O(CH$_2$)$_4$—O—(CH$_2$)$_4$—O—CH$_3$ with a viscosity of 2.3 cp In a 2 liter three-neck flask topped by a cooler and a bromine flask, 99.5 g (0.5M) of dichloro-4,4' dibutylether are dissolved in 1.5 liters of anhydrous methanol. 108.04 g (2M) of sodium methylate are then gradually added. At the end of the addition, the heterogeneous solution is subjected to a methanol flow under agitation for 48 hours.

After cooling, the precipitate is filtered then washed with methanol. After the filtrates are concentrated 1 to 10, the filtering process is repeated, then the methanol solution is precipitated in 500 ml of a water and ice mixture. Extraction is performed using methylene chloride, then the product is dried on anhydrous sodium sulfate. After evaporation of the methylene chloride, 84.3 g of an oil is obtained (yield: 88.8%). Distillation at 79°–80° C. produces 61.6 g of the expected product (yield; 64.9%). The structure of the dimethoxy-4,4' dibutylether is confirmed by:
RMN 62 MH$_z$ $^{13}$C
Mass spectrometry: electronic impact; chemical ionization.

Example 10

Diisoamyl ether from polytetrahydrofuran of formula

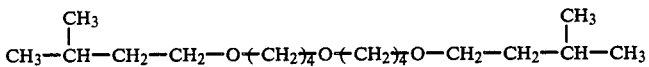

with a viscosity of 5.7 cp

In a 2 liter reactor, 352 g of isoamylic alcohol, 320 g of aqueous soda at 50% and 81.5 g of tetrabutylammonium hydrogen sulfate are introduced.

The mixture is brought to 70° C. under agitation and 199 g of dichloro-4,4' dibutyl ether are introduced over a three-hour period.

The mixture is then brought to 90° C. and kept at that temperature for 2 hours.

The organic phase is cooled to 20° C., washed with water several times, then dried on anhydrous sodium sulfate. Fractional distillation is then performed. The result is 136.8 g of a fraction with a boiling point of 116° C.–118° C. under 0.3 mm of Hg, corresponding to the expected product (structure confirmed by RMN$^{13}$C, mass spectrometry, elemental analysis andIR spectroscopy). The compound is displayed in the form of a colorless liquid which is insoluble in water, with a viscosity of 5.7 cp and a solidification point of less than −60° C.

Example 11

Dihexyl ether from polytetrahydrofuran of formula:
CH$_3$—(CH$_2$)$_4$—CH$_2$—O—(CH$_2$)$_4$—O—(CH$_2$)$_4$—O—CH$_2$—(CH$_2$)$_4$—CH$_3$ with a viscosity of 6.9 cp The same procedure as described in Example 10 is followed, replacing the isoamylic alcohol with 408 g of 1-hexanol. Fractional distillation produces 173 g of a fraction having a boiling point of 146°–148° C. under 0.35 mm of Hg. Mass spectroscopy, RMN$^{13}$C spectroscopy, elemental analysis and IR spectroscopy confirm the anticipated structure. The product is a colorless oil, which is insoluble in water, with a viscosity of 6.9 cp and a solidification point of −9.5° C.

Example 12

Dioctyl ether from polytetrahydrofuran of formula:
CH$_3$—(CH$_2$)$_6$—CH$_2$—O—(CH$_2$)$_4$—O—(CH$_2$)$_4$—O—CH$_2$—(CH$_2$)$_6$—CH$_3$ and a viscosity of 11 cp In a 2-liter reactor, 390 g of 1-octanol and 480 g of aqueous soda at 50% are introduced. 61 g of tetrabutyl ammonium hydrogen sulfate are added and the mixture is brought to 65° C. under agitation. 199 g of dichloro-4,4' dibutylether are introduced over a three hour period, and the mixture is kept at 65° C. for two additional hours. The organic phase is washed with water, dried on anhydrous sodium sulfate, and fractional distillation is performed under vacuum. 193 g of a fraction with a boiling point of 180° C. under 0.2 mm of Hg are obtained, corresponding to the anticipated compound (structure and purity confirmed by mass spectrometry, RMN$^{13}$C spectrometry, elemental analysis and IR spectroscopy). The product is a colorless liquid, which is insoluble in water, with a viscosity of 11 cp and a solidification point of 8.6° C.

Example 13

Di(2-ethyl hexyl)ether from polytetrahydrofuran of formula

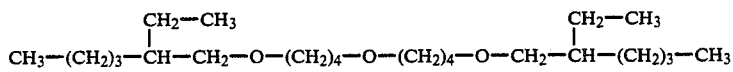

with a viscosity of 10 cp

The same procedure as described in Example 10 is followed, replacing the isoamylic alcohol with 520 g of 2-ethyl 1-hexanol. After processing, fractional distillation results in 116 g of a fraction with a boiling point of 150° C. under 0.2 mm of Hg. Mass spectrometry, RMN$^{13}$C spectroscopy, elemental analysis and IR spectroscopy confirm the anticipated structure. The compound is in the form of a colorless liquid which is insoluble in water, with a viscosity of 10 cp.

| EXAMPLES OF COMPOSITIONS | |
|---|---|
| Example 1: FOUNDATION | |
| Stearin | 2.50 g |
| Diethylene glycol stearate | 0.50 g |
| Glycerol mono/distearate | 2.00 g |
| Propyl parahydroxybenzoate | 0.10 g |
| Compound from Example 1 | 15.00 g |
| Propylene glycol | 3.00 g |
| Glycerin | 2.00 g |
| Magnesium silicoalminate | 1.00 g |
| Mineral pigments | 9.00 g |
| Triethanolamine | 1.10 g |
| Xanthan gum | 0.10 g |
| Methyl Parahydroxybenzoate | 0.10 g |
| Fragrance | 0.30 g |
| Sufficient quantity of water for | 100 g |
| Example 2: TINTED CREAM | |
| Stearin | 2.00 g |
| Diethylene glycol stearate | 2.00 g |
| Compound from Example 2 | 10.00 g |
| Propylene glycol | 5.00 g |
| Magnesium silicoaluminate | 1.00 g |
| Mineral pigments | 5.00 g |
| Triethanolamine | 0.90 g |
| Volatile silicone | 13.00 g |
| Polyethylene powder | 5.00 g |
| Fragrance | 0.30 g |
| Sufficient quantity of water and preservative for | 100 g |
| Example 3: EYE SHADOW (in the form of a water-in-oil emulsion) | |
| Esters of fatty acids and of Sorbitan | 4.00 g |
| Microcrystalline wax | 5.00 g |

EXAMPLES OF COMPOSITIONS -continued

| | |
|---|---|
| Beeswax | 2.00 g |
| Paraffin Oil | 4.00 g |
| Compound from Example 3 | 4.00 g |
| Titanium mica | 2.00 g |
| Red Iron Oxide | 0.50 g |
| Polyethylene powder | 5.00 g |
| Sufficient quantity of water and preservative for | 100 g |

Example 4: ROUGE

| | |
|---|---|
| Carnauba wax | 18.00 g |
| Paraffin | 10.00 g |
| Fatty acid triglycerides | 26.60 g |
| Compound from Example 1 | 30.00 g |
| Talcum | 5.00 g |
| Zinc stearate | 5.00 g |
| Butylated hydroxy toluene | 0.10 g |
| Titanium dioxide | 4.00 g |
| D & C Red No. 7 | 0.30 g |
| Yellow Iron Oxide | 1.00 g |

Example 5: MASCARA

| | |
|---|---|
| Triethanolamine stearate | 12.00 g |
| Carnauba wax | 10.00 g |
| Candelilla wax | 9.00 g |
| Xanthan gum | 1.00 g |
| Black Iron Oxide | 10.00 g |
| Compound from Example 2 | 10.00 g |
| Sufficient quantity of preservative and water for | 100 g |

Example 6: POWDER EYESHADOW

| | |
|---|---|
| Titanium Mica | 30.00 g |
| Mineral pigments | 18.00 g |
| Oil of paraffin | 6.00 g |
| Isopropyl myristate | 1.00 g |
| Lanolin | 0.50 g |
| Compound from Example 2 | 2.00 g |
| Preservative | 0.20 g |
| Sufficient quantity of talcum for | 100 g |

Example 7: ANHYDROUS FACE CREAM

| | |
|---|---|
| Petrolatum | 30.00 g |
| Perhydrosqualene | 10.00 g |
| Compound from Example 3 | 20.00 g |
| Bentone gel | 15.00 g |
| Grapeseed oil | 10.00 g |
| Paraffin oil | 14.45 g |
| BHA | 0.05 g |
| Fragrance | 0.50 g |

Example 8: PROTECTIVE DAY CREAM

| | |
|---|---|
| Self-emulsifying glycerol stearate | 3.00 g |
| Cetyl alcohol | 0.50 g |
| Stearyl alcohol | 0.50 g |
| Compound from Example 2 | 15.00 g |
| Sesame oil | 10.00 g |
| Stearic acid | 3.00 g |
| Hydroxy-2 methoxy-4 benzophenone (sunscreen) | 1.00 g |
| Glycerin | 5.00 g |
| Methyl parahydroxybenzoate | 0.30 g |
| Sufficient quantity of demineralized water for | 100 g |

Example 9: PROTECTIVE MOISTURIZING CREAM

| | |
|---|---|
| Mg Lanolate | 3.00 g |
| Lanolin alcohol | 5.00 g |
| Petrolatum | 15.00 g |
| Paraffin oil | 17.00 g |
| Compound from example 3 | 12.00 g |
| Methyl parahydroxybenzoate | 0.30 g |
| Sufficient quantity of demeralized water for | 100 g |

Example 10: MOISTURIZING BODY LOTION EMULSION

| | |
|---|---|
| Polyethylene glycol stearate with 20 moles of ethylene oxide | 2.00 g |
| Self-emulsifying glycerol stearate | 1.20 g |
| Stearyl alcohol | 1.00 g |
| Compound from Example 1 | 8.00 g |
| Soybean oil | 3.00 g |
| Lanolin alcohol | 3.00 g |
| Glycerin | 3.00 g |
| Methyl parahydrobenzoate | 0.30 g |
| Fragrance | 0.30 g |
| Sufficient quantity of demineralized water for | 100 g |

Example 11: PROTECTIVE HAND CREAM

| | |
|---|---|
| Oxyethylenated Sorbitan monostearate with 20 moles of ethylene oxide | 2.00 g |
| Cetyl alcohol | 1.00 g |
| Compound from Example 2 | 10.00 g |
| Silicone oil | 7.00 g |
| Propylene glycol | 2.00 g |
| Carboxyvinyl polymer | 0.30 g |
| Triethanolamine | 0.30 g |
| Methyl parahydroxybenzoate | 0.30 g |
| Sufficient quantity of demineralized water for | 100 g |

Example 12: NOURISHING MOISTURIZING NIGHT CREAM

| | |
|---|---|
| Mg Lanolate | 3.40 g |
| Lanolin alcohol | 2.80 g |
| Perhydrosqualene | 10.00 g |
| Compound from Example 1 | 20.00 g |
| Sesame oil | 10.00 g |
| Paraffin oil | 8.80 g |
| Methyl parahydroxybenzoate | 0.30 g |
| Glycerin | 3.00 g |
| Polytissue extracts | 2.00 g |
| Fragrance | 0.30 g |
| Sufficient quantity of demineralized water for | 100 g |

Example 14: BODY CREAM

| | |
|---|---|
| Cetylic alcohol | 1.20 g |
| Glycerol monostearate | 4.80 g |
| Compound from Example 1 | 10.00 g |
| Paraffin oil | 20.00 g |
| Carboxyvinyl polymer | 0.40 g |
| Triethanolamine | 0.40 g |
| Disodium salt of carboxymethyl-1 hydroxide (carboxymethyl-oxy-2 ethyl)undecyl-2 imidazolinium) | 4.00 g |
| Preservative | 0.05 g |
| Fragrance | 0.10 g |
| Sufficient quantity of demineralized water for | 100 g |

Example 15: CLEANSING LOTION

| | |
|---|---|
| Stearic acid | 5.00 g |
| Triethinolamine | 2.50 g |
| Cetyl alcohol | 1.00 g |
| Compound from Example 2 | 12.00 g |
| Oxyethylene glycerol monostearate with 20 moles of ethylene oxide | 3.00 g |
| Methyl parahydroxybenzoate | 0.30 g |
| Sufficient quantity of demineralized water for | 100 g |

EXAMPLE 16: CLEANSING CREAM

| | |
|---|---|
| Stearic Acid | 3.00 g |
| Cetylic alcohol | 3.00 g |
| Self-emulsifing glycerol monostearate | 6.00 g |
| Compound from Example 3 | 10.00 g |
| Paraffin oil | 20.00 g |
| Propylene glycol | 2.50 g |
| Triethanolamine | 1.00 g |
| Methyl parahydroxybenzoate | 0.30 g |
| Sufficient quantity of demineralized water for | 100 g |

Example 17: MOISTURIZING MASK

| | |
|---|---|
| Stearic acid | 10.00 g |
| Triethanolamine | 2.50 g |
| Cetyl alcohol | 2.50 g |
| Kaolin | 15.00 g |
| Glycerin | 5.00 g |
| Compound from Example 3 | 15.00 g |
| Methyl parahydroxybenzoate | 0.30 g |
| Fragrance | 0.30 g |
| Sufficient quantity of demineralized water for | 100 g |

Example 18: SUNTAN CREAM (in the form of an oil-in-water emulsion)

| | |
|---|---|
| Compound from example 3 | 30.00 g |
| Hydrogenated copra oil | 18.00 g |

EXAMPLES OF COMPOSITIONS -continued

| | |
|---|---|
| Carboxymethyl cellulose | 0.40 g |
| Sorbitan stearate | 3.00 g |
| Sorbitan stearate with 20 moles of ethylene oxide | 4.00 g |
| Glycerin | 5.00 g |
| Ethyl-2-hexyl p. methoxycinnamate | 3.00 g |
| Preservative | 0.50 g |
| Fragrance | 0.10 g |
| Sufficient quantity of water for | 100 g |

Example 19: TANNING CREAM (in emulsion form)

| | |
|---|---|
| Compound from Example 4 | 11.50 g |
| Mixture of glyceryl oleate and propylene glycol | 3.00 g |
| Beeswax | 1.00 g |
| Sorbitol at 70% | 28.00 g |
| Ceresin | 1.00 g |
| Methyl parahydroxybenzoate | 0.20 g |
| Fragrance | 0.05 g |
| Sufficient quantity of water for | 100 g |

Example 20: SUNSCREEN OIL

| | |
|---|---|
| Compound from Example 3 | 68.00 g |
| Olive oil | 15.00 g |
| Isopropyl myristate | 12.00 g |
| Lanolin oil | 2.00 g |
| Homomenthyl salicylate | 3.00 g |

Example 21: SUNTAN LOTION

| | |
|---|---|
| Compound from Example 1 | 2.00 g |
| Compound from Example 2 | 2.50 g |
| Stearic acid | 2.50 g |
| DC 2000 dimethyl polysiloxane | 1.50 g |
| Glycerin | 5.00 g |
| Acetylated lanolin | 1.00 g |
| Lanolin alcohol | 7.00 g |
| Triethanolamine | 1.00 g |
| Benzylidene-3 camphor | 4.00 g |
| Glyceryl monostearate | 2.00 g |
| Methyl parahydroxybenzoate | 0.10 g |
| Propyl parahydroxybenzoate | 0.05 g |
| Sufficient quantity of water for | 100 g |

Example 22: HAIR DYE COMPOSITION WITH OXIDATION COLORING AGENTS

| | |
|---|---|
| Compound from Example 1 | 2.00 g |
| Glycerolated oleic alcohol with 2 moles of glycerol | 4.70 g |
| Glycerolated oleic alcohol with 4 moles of glycerol | 4.70 g |
| Oleic acid | 4.70 g |
| Oleic diethanolamide | 4.70 g |
| Oleic diethanolanide | 11.50 g |
| Ethyl alcohol | 10.00 g |
| Monoethylether of ethylene glycol | 12.00 g |
| Diaminotetracetic ethylene acid | 0.20 g |
| Ammonia at 20° Be | 10.00 g |
| Dichlorhydrate of methyl-2 diamino-1,4 benzene | 0.64 g |
| Amino-1 hydroxy-4 benzene | 0.10 g |
| Dihydroxy-1,3 benzene | 0.20 g |
| Hydroxy-1 amino-3 benzene | 0.06 g |
| Amino-6 benzomorpholine dichlorhydrate | 0.045 g |
| Hydroquinone | 0.15 g |
| Sodium bisulfite at 35° Be | 1.30 g |
| Sufficient quantity of water for | 100 g |

At the time of application, this composition is diluted, weight for weight, with hydrogen peroxide at 20 volumes and is applied to the hair. It confers a light ash chestnut color.

Example 23: HAIR DYE COMPOSITION WITH A DIRECT TINT BASE

| | |
|---|---|
| Compound from Example 3 | 1.50 g |
| Monoethylether of ethylene glycol | 3.50 g |
| Lauric diethanolamide | 1.50 g |
| Lauric acid | 2.00 g |
| Methyl parahdyroxybenzoate | 0.10 g |
| Propyl parahydroxybenzoate | 0.05 g |
| Hydroxyethylcellulose | 1.00 g |
| Methoxy-3 N—-hydroxyethylamine-4 nitrobenzene | 0.10 g |
| N—β-hydroxyethylamino-2 hydroxy-5 nitrobenzene | 0.40 g |
| Amino-2 hydroxy-5 nitrobenzene | 0.10 g |
| Amino-2 methyl-2 propanol 1 in sufficient quantity for | pH 9.5 |
| Sufficient quantity of water for | 100 g |

This composition, when applied to the hair, produces a coppery red shade.

Example 24: SHAMPOO

| | |
|---|---|
| Compound from Example 4 | 1.00 g |
| Triethanolamine sulfate alcoyl (C12–C14) with 40% active ingredient | 8.00 g |
| Compound of formula: | |

$$RC(O)-NH-CH_2-CH_2-N^+(CH_2-CH_2-OH)(CH_2COONa)-CH_2-COO^-$$

| | |
|---|---|
| where RCO represents the remaining coprah acid | 3.80 g |
| Chlorhydric acid sufficient for | pH 7.3 |
| Sufficient quantities of water + (fragrance, preservative and tint) for | 100 g |

Example 25: ANIONIC SHAMPOO

| | |
|---|---|
| Compound from Example 4 | 1.00 g |
| Alkyl (C12-C14) ether sodium sulfate, oxyethylenated at 2.2 moles of ethylene oxide. 25% active ingredient | 10.00 g |
| Lauryl diethanolamide | 1.00 g |
| Sodium hydroxide in sufficient quantity for | pH 7.6 |
| Sufficient quantities of water + (fragrance, preservative and tint) for | 100 g |

Example 26: NON-IONIC SHAMPOO

| | |
|---|---|
| Compound from Example 2 | 0.5 g |
| Compound of formula: R—CHOH—CH$_2$—O(CH$_2$—CHOH—CH$_2$—O)n H. R: mixture of alkyl radicals in C9-C12 n: represents an average statistical value of about 3.5 | 10.00 g |
| Glucoside alkyl ether with 30% active ingredient | 1.00 g |
| Sodium hydroxide in sufficient quantity for | pH 7 |
| Sufficient quantities of water + (fragrance, preservative, coloring agent) for | 100 g |

Example 27: RINSE

| | |
|---|---|
| Compound from Example 1 | 0.50 g |
| Quaternary cellulose derivative | 0.50 g |
| Dimethyl distearyl ammonium chloride | 0.60 g |
| Hydroxyethylcellulose | 1.00 g |
| Sufficient quantity of sodium hydroxide for | pH 8 |
| Sufficient quantity of water + (fragrance, preservative, coloring agent) for | 100 g |

Example 28: HAIR CONDITIONER

| | |
|---|---|
| Compound from Example 2 | 0.50 g |
| Compound of formula: CH$_3$—(CH$_2$)$_{11}$—CH$_2$—(O—CH$_2$—CH$_2$)$_6$—OCH$_2$—COONa | 2.00 g |
| Sufficient quantity of sodium hydroxide for | pH 7.7 |
| Stearyldimethylbenzylammonium chloride | 1.00 g |
| Sufficient quantity of water for | 100 g |

This composition is packaged in aerosol form, at 10% in a freon 12/114 (53/47) mixture.

Example 29: BRONZING GEL FOR THE LEGS

| | |
|---|---|
| Carboxyvinyl polymer | 1.00 g |
| 20% triethanolamine | 0.70 g |
| 95% ethanol | 40.00 g |
| Compound of Example 6 | 5.00 g |
| -carotene | 2.00 g |
| Sufficient quantity of water for | 100 g |

Example 30: DRY SKIN CREAM

| | |
|---|---|
| Solid petrolatum fraction | 50.00 g |
| Compound from Example 1 | 50.00 g |

Example 31: MASSAGE OIL

| | |
|---|---|
| Triglycerides of octanoic and decanoic acids | 15.00 g |
| Volatile silicone | 20.00 g |
| Mixture of glycol stearate and polyethylene glycol stearate | 1.50 g |

| | |
|---|---|
| -continued | |
| Non denatured absolute alcohol | 15.00 g |
| Camphor | 0.05 g |
| Menthol | 0.15 g |
| Preservative | 0.20 g |
| Butylated hydroxytoluene | 0.15 g |
| Vegetable oil compounds (mixture of paraffin oil, oils of almond, apricot and arnica) | 3.00 g |
| Oil of lavender | 2.00 g |
| Sufficient quantity of compound from Example 2 for | 100 g |
| Example 32: ACNE LOTION | |
| Non denatured absolute alcohol | 50.00 g |
| Compound from Example 1 | 50.00 g |
| Butylated hydroxyanisole | 0.05 g |
| Vitamin A acid | 0.06 g |
| Example 33: EMULSION WITH A BENZOYL PEROXIDE BASE FOR TREATMENT OF ACNE | |
| Polyethylene glycol stearate with 20 moles of O.E. | 3.85 g |
| Glycerol mono and distearate | 0.7 g |
| Mixture of ceto-stearyl alcohol and sodium alkyl sulfate | 4.00 g |
| Cetyl alcohol | 2.45 g |
| Compound from Example 1 | 10.00 g |
| Anti-foaming agent | 0.2 g |
| Carboxyvinylic polymer sold by Goodrich under the trade name "CARBOPOL 941" | 0.2 g |
| Benzoyl peroxide (active ingredient) | 10.00 g |
| Preservative | 0.224 g |
| Bactericide | 0.3 g |
| 20% triethanolamine | 1.00 g |
| Sufficient quantity of sterile, demineralized water for | 100 g |
| Example 34: ANTHRALIN GEL | |
| Compound from Example 1 | 55.50 g |
| Gantrez ES 425 resin | 42.50 g |
| Anthralin | 0.50 g |
| Example 35: THIOXOLONE LOTION | |
| Absolute alcohol | 40.00 g |
| Thioxolone | 0.50 g |
| Sufficient quantity of compound from Example 1 for | 100 g |
| Example 36: ERYTHROMYCIN LOTION | |
| Absolute alcohol | 30.00 g |
| Triglycerides of octanoic and decanoic acids | 20.00 g |
| Compound from Example 2 | 48.00 g |
| Erythromycin | 2.00 g |

We claim:

1. A cosmetic method for producing on the skin a matte film which is not greasy and for imparting a protective and emollient effect on the skin which comprises topically applying to the skin an effective amount of a cosmetic composition containing a fatty product, said fatty product being a polyether oligomer, having the formula

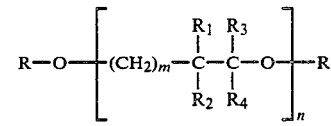

wherein

R represents linear or branched alkyl having 1-12 carbon atoms, $R_1$, $R_2$, $R_3$ and $R_4$ each independently represent hydrogen or alkyl having 1-6 carbon atoms, wherein at least two of $R_1$, $R_2$, $R_3$ and $R_4$ represent hydrogen, m is 1-4 and n has an average value equal to or greater than 2, the number of carbon atoms in each repetitive unit being at least equal to 4, said polyether oligomer having a molecular weight ranging from 200 to 5,000.

2. The method of claim 1 wherein R represents methyl, ethyl, butyl, hexyl or lauryl.

3. The method of claim 1 wherein R represents methyl, ethyl or butyl, $R_1$ to $R_4$ represent hydrogen and m is 2.

4. The method of claim 1 wherein the viscosity of said polyether oligomer ranges from 2 to 1,000 centipoises at 25° C.

5. The method of claim 1 wherein said polyether oligomer is dimethyl ether of polytetrahydrofuran having the formula

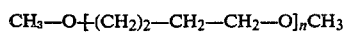

wherein n has an average value ranging from 4 to 10.

6. The method of claim 1 wherein said polyether oligomer is present in an amount ranging from 0.5 to 99 percent by weight based on the total weight of said composition.

7. The method of claim 1 wherein said polyether oligomer is present in an amount ranging from 5 to 50 percent by weight based on the total weight of said composition.

* * * * *